United States Patent
Masciale et al.

(10) Patent No.: US 8,979,906 B2
(45) Date of Patent: Mar. 17, 2015

(54) SPINE ROD CLAMPING BODY AND PEDICLE SCREW ASSEMBLY COMPRISING SAME

(71) Applicants: John Masciale, Corpus Christi, TX (US); Timothy W. Hildebrand, Austin, TX (US)

(72) Inventors: John Masciale, Corpus Christi, TX (US); Timothy W. Hildebrand, Austin, TX (US)

(73) Assignee: OMNI Acquisition, Inc., Marietta, GA (US)

( * ) Notice: Subject to any disclaimer, the term of this patent is extended or adjusted under 35 U.S.C. 154(b) by 156 days.

(21) Appl. No.: 13/686,632

(22) Filed: Nov. 27, 2012

(65) Prior Publication Data
US 2014/0148857 A1    May 29, 2014

(51) Int. Cl.
*A61B 17/70* (2006.01)
(52) U.S. Cl.
CPC .................................. *A61B 17/7032* (2013.01)
USPC .................................................................. 606/266
(58) Field of Classification Search
USPC .................. 606/246, 264–279; 411/392, 544
See application file for complete search history.

(56) References Cited

U.S. PATENT DOCUMENTS

| 8,114,141 | B2 | 2/2012 | Appenzeller |
| 2006/0173456 | A1 | 8/2006 | Hawkes |
| 2008/0306536 | A1* | 12/2008 | Frigg et al. ..................... 606/246 |
| 2010/0100137 | A1 | 4/2010 | Justis |
| 2011/0257687 | A1* | 10/2011 | Trieu et al. ..................... 606/267 |
| 2012/0053635 | A1* | 3/2012 | Trieu et al. ..................... 606/254 |
| 2013/0338721 | A1* | 12/2013 | Biedermann et al. .......... 606/305 |

OTHER PUBLICATIONS

Bellows. Dictionary.com. Dictionary.com Unabridged. Random House, Inc. http://dictionary.reference.com/browse/bellows (accessed: Dec. 1, 2014).*

* cited by examiner

*Primary Examiner* — Jan Christopher Merene
*Assistant Examiner* — Steven Cotroneo
(74) *Attorney, Agent, or Firm* — David O. Simmons

(57) ABSTRACT

A pedicle screw assembly having a spine rod clamping body designed for exhibiting a limited amount of elastic deformation at a region location between its spine rod mounting portion and its bone screw connecting portion. When the pedicle screw assembly is placed in a spine stabilization procedure, a limited amount of motion within the fixation apparatus as a result of the spine rod clamping body exhibiting a limited amount of elastic deformation at the region location between its spine rod mounting portion and its bone screw connecting portion. This limited amount of motion can accelerate bone fusion. By reducing movement-induced stress concentrations, the limited amount of elastic deformation provided by the spine rod clamping body can enhance a rate at which bone fusion progresses and can reduce the potential for damage to the interface between the bone screw and bone.

13 Claims, 1 Drawing Sheet

SPINE ROD CLAMPING BODY AND PEDICLE SCREW ASSEMBLY COMPRISING SAME

FIELD OF THE DISCLOSURE

The disclosures made herein relate generally to pedicle screw assemblies and, more particularly, to a pedicle screw body (i.e., spine rod clamping body) exhibiting a limited amount of elastic deformation at a region location between its spine rod mounting portion and its bone screw connecting portion.

BACKGROUND

The spinal column is a highly complex system of bones (i.e., vertebral bodies) and connective tissues that provides support for the body and protects the delicate spinal cord and nerves. The spinal column includes a series of vertebrae stacked one atop the other, each vertebral body including an inner or central portion of relatively weak cancellous bone and an outer portion of relatively strong cortical bone. Situated between each vertebral body is an intervertebral disc that cushions and dampens compressive forces on the spinal column. A vertebral canal containing the spinal cord and nerves is located within the forward-facing surface of the vertebral bodies.

There are many types of spinal column disorders. Patients that suffer from such disorders typically experience extreme and debilitating pain, as well as diminished nerve function. Examples of such spinal column disorders include, but are not limited to, scoliosis (i.e., abnormal lateral curvature of the spine), kyphosis (i.e., abnormal forward curvature usually in the thoracic portion of the spine), excess lordosis (i.e., abnormal backward curvature usually in the lumbar portion of the spine), spondylolisthesis (forward displacement of one vertebrae over another usually in the lumbar portion or cervical portion of the spine), etc. There are still other types of spinal column disorders caused by physiological abnormalities, disease and/or trauma such as, for example, ruptured or slipped discs, degenerative disc disease, fractured vertebra, and the like.

Multi-segmental spinal fixation is an accepted surgical procedure in the treatment of such spinal column disorders. It involves the use of a series of pedicle screw assemblies and one or more spine rods. The pedicle screw assemblies each include a screw that is threadedly screwed into one of a plurality of adjacent vertebral bodies. A spine rod (contoured or straight) is fixedly secured to a spine rod clamping body of each one of the pedicle screws for fixing two or more adjacent vertebral bodies in a static relative position. In this manner, spinal fixation can be used to alter the alignment of adjacent vertebrae relative to one another so as to change the overall alignment of the spine, to preclude relative movement between adjacent vertebrae, and the like.

Rigid fixation resulting from pedicle screw assemblies and attached spine rods that inhibit flexure within the spine rod clamping body, the spine rod and interface therebetween can result in stresses that are placed on the fixation system and attached bone structure after implantation of the fixation system such as, for example, resulting from normal activity of the patient. These stresses can adversely impact several aspects of the bone fusion process. In particular, these stresses can adversely impact a rate at which such bone fusion progresses and can result in damage to the interface between the bone screw and bone from overstressing of such bone-to-screw interface prior to such bone fusion progressing to a sufficient level.

Therefore, a pedicle screw assembly having a spine rod clamping body that exhibits a limited amount of elastic deformation at a region location between its spine rod mounting portion and its bone screw connecting portion would be advantageous, desirable and useful.

SUMMARY OF THE DISCLOSURE

Embodiments of the present invention are directed to a spine rod clamping body (i.e., pedicle screw body) that exhibits a limited amount of elastic deformation at a region location between its spine rod mounting portion and its bone screw connecting portion. When a pedicle screw assembly having such a spine rod clamping body is placed in a spine fixation procedure, a limited amount of motion within the fixation apparatus (i.e., pedicle screw assemblies coupled to a spine rod) is provided as a result of the spine rod clamping body exhibiting a limited amount of elastic deformation at the region location between its spine rod mounting portion and its bone screw connecting portion. By reducing movement-induced stress concentrations/impulses, pedicle screw assemblies having a spine rod clamping body configured in accordance with the present invention can contribute to enhancing a rate at which bone fusion progresses and reducing the potential for damage to the interface between the bone screw and bone from overstressing of such bone-to-screw interface prior to such bone fusion progressing to a sufficient level.

In one embodiment of the present invention, a spine rod clamping body for a pedicle screw assembly comprises a spine rod mounting portion, a bone screw connecting portion, and an elastically deformable portion connected between the spine rod mounting portion and the bone screw connecting portion. The elastically deformable portion, the bone screw connecting portion and the spine rod mounting portion are all concentric about a common central axis. The elastically deformable portion includes a plurality of spaced apart ring structures and a circular bridge structure. Each one of the spaced apart ring structures has a semi-circular cross sectional profile. The circular bridge structure joins adjacent ones of the hollow ring such that adjacent ones of the spaced apart ring structures and the circular bridge structure therebetween jointly form a structure that is elastically deformable.

In another embodiment of the present invention, a pedicle screw assembly comprises a spine rod clamping body and a bone screw. The spine rod clamping body includes a spine rod mounting portion, a bone screw connecting portion, and an elastically deformable portion between the spine rod mounting portion and the bone screw connecting portion. The elastically deformable portion, the bone screw connecting portion and the spine rod mounting portion are all formed as a one-piece structure from a single piece of material and are all concentric about a common central axis. The elastically deformable portion includes a plurality of spaced apart ring structures and a circular bridge structure joining adjacent ones of the ring such that adjacent ones of the spaced apart ring structures and the circular bridge structure therebetween jointly form a structure that elastically deforms when a bending moment is exerted between the spine rod mounting portion and the bone screw connecting portion. Each one of the spaced apart ring structures has a u-shaped cross-sectional profile. The bone screw has a first end portion and a second end portion. The first end portion is connected to the bone screw coupling portion of the spine rod clamping body. The second end portion defines a tip portion of the bone screw.

In another embodiment of the present invention, a polyaxial pedicle screw assembly, comprises a spine rod clamping body and a bone screw. The spine rod clamping body includes a spine rod mounting portion, a bone screw connecting portion, and an elastically deformable portion between the spine rod mounting portion and the bone screw connecting portion. The elastically deformable portion, the bone screw connecting portion and the spine rod mounting portion are all formed as a one-piece structure from a single piece of material and are all concentric about a common central axis. The elastically deformable portion includes a plurality of spaced apart annular structures and a circular bridge structure joining adjacent ones of the spaced apart annular structures such that adjacent ones of the spaced apart annular structures and the circular bridge structure therebetween jointly form a structure that elastically deforms when a bending moment is exerted between the spine rod mounting portion and the bone screw connecting portion. Each one of the spaced apart annular structures has a u-shaped cross-sectional profile. The bone screw has a tip portion and a head portion. The head portion is pivotably coupled to the bone screw coupling portion of the spine rod clamping body.

These and other objects, embodiments, advantages and/or distinctions of the present invention will become readily apparent upon further review of the following specification, associated drawings and appended claims.

DETAILED DESCRIPTION OF THE DRAWING FIGURES

Figure 1:
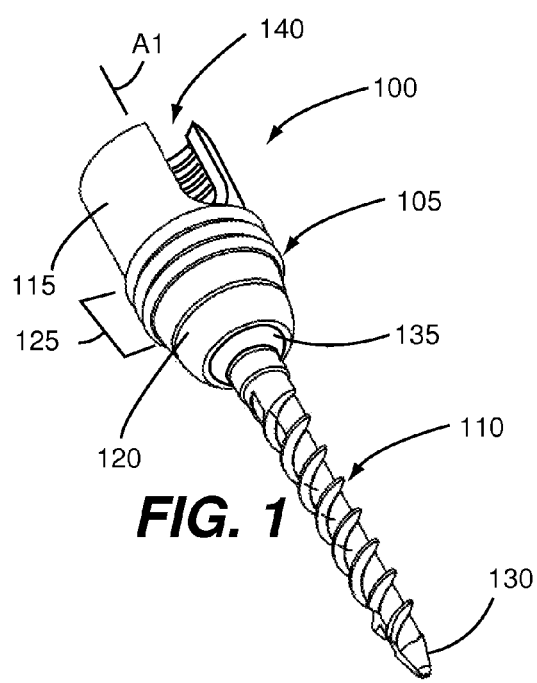
FIG. 1 is a perspective view of a polyaxial pedicle screw assembly configured in accordance with an embodiment of the present invention.
Figure 2:
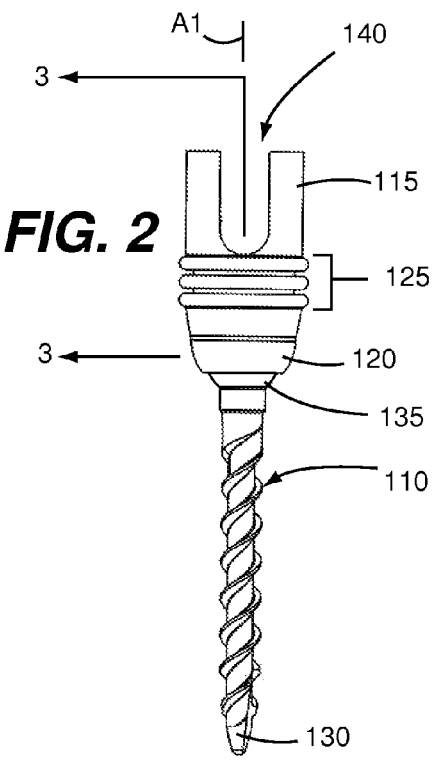
FIG. 2 is a side view of the polyaxial pedicle screw assembly of FIG. 1.
Figure 3:
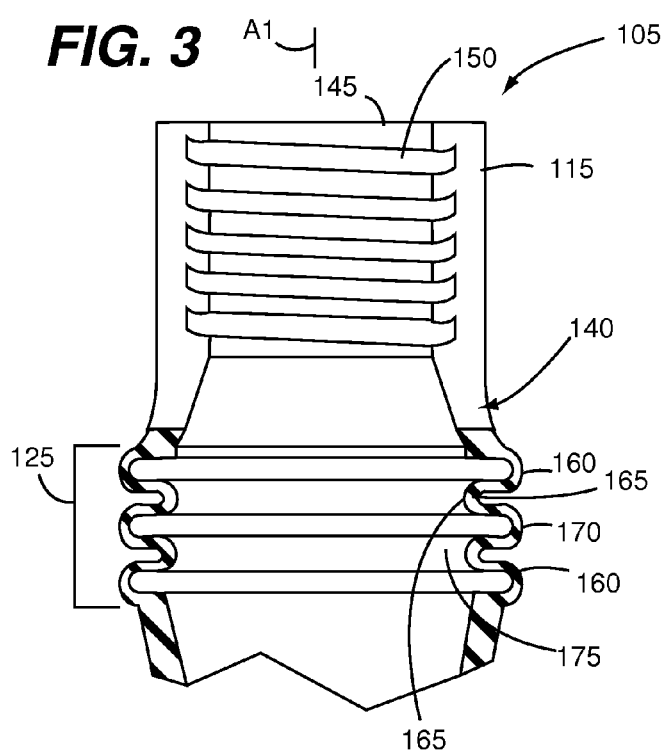
FIG. 3 is a cross-sectional view taken along the line 3-3 in FIG. 2.

FIGS. 1-3 show a poly-axial pedicle screw assembly 100 configured in accordance with an embodiment of the present invention. The polyaxial pedicle screw assembly 100 includes a spine rod clamping body 105 and a bone screw 110. The spine rod clamping body 105 includes a spine rod mounting portion 115, a bone screw connecting portion 120, and an elastically deformable portion 125 between the spine rod mounting portion 115 and the bone screw connecting portion 120. Examples of suitable materials from which the spine rod clamping body 105 and/or the bone screw 110 can be made include, but are not limited to, stainless steel alloy, titanium alloy, and cobalt chrome alloy.

The bone screw 110 has a tip portion 130 and a head portion 135. The head portion 135 is pivotably coupled to the bone screw coupling portion 120 of the spine rod clamping body 105 by a known coupling arrangement. For example, the head portion 135 can be spherical in shape and captured within a mating spherical seat of the bone screw coupling portion 120. It is discloses herein that embodiments of the present invention are not unnecessarily limited to any particular arrangement for pivotably coupling the bone screw 110 to the spine rod clamping body 105.

The spine rod mounting portion 115 has a spine rod receiving channel 140 extending therethrough. As best shown in FIG. 3, interior side walls 145 have threads 150 formed therein. The threads 150 are configured for engaging mating threads of a setscrew used for securing a spine rod within the spine rod receiving channel 140.

The spine rod mounting portion 115, the bone screw connecting portion 120, and the elastically deformable portion 125 are preferably all formed as a one-piece structure from a single piece of material. Alternatively, the spine rod mounting portion 115, the bone screw connecting portion 120, or the elastically deformable portion 125 (i.e., spine rod clamping body components) can be an individual component rigidly connected to the adjacent spine rod clamping body component(s). The spine rod mounting portion 115, the bone screw connecting portion 120, and the elastically deformable portion 125 are all concentric about a common central axis A1.

In use (i.e., when placed in a spine fixation procedure), the poly-axial pedicle screw assembly 100 provides for a limited amount of motion within the fixation apparatus (i.e., pedicle screw assemblies coupled to a spine rod). Specifically, a limited amount of motion within the fixation apparatus is provided as a result of the spine rod clamping body 105 exhibiting a limited amount of elastic deformation within the elastically deformable portion 125 when the spine rod clamping body 105 is loaded (e.g., by a bending force generated between the spine rod mounting portion 115 and the bone screw connecting portion 120), and will thereafter return to its original shape/configuration when the loading is removed. The amount of motion is can be relatively small such as, for example, up to about 2 degrees of deflection between the spine rod mounting portion 115 and the bone screw connecting portion 120 for a typical/anticipated maximum loading. By reducing these movement-induced stress concentrations/impulses, the poly-axial pedicle screw assembly 100 can contribute to enhancing a rate at which bone fusion progresses and reducing the potential for damage to the interface between the bone screw and bone from overstressing of such bone-to-screw interface prior to such bone fusion progressing to a sufficient level. Once bone fusion is complete (or suitably progressed), the polyaxial pedicle screw assembly 100 becomes effectively passive (i.e., no longer subjected to applied forces that would cause elastic deformation).

Referring now to FIG. 3, the elastically deformable portion 125 includes a plurality of spaced apart annular structures 160 and a circular bridge structure 165 joining adjacent ones of the spaced apart annular structures. In this regard, adjacent ones of the spaced apart annular structures 160 and the circular bridge structure 165 therebetween jointly form a structure that elastically deforms when a suitable load (e.g., a bending moment) is exerted between the spine rod mounting portion 115 and the bone screw connecting portion 120.

Each one of the spaced apart annular structures 160 can be embodied as a ring structure having a semi-circular cross sectional profile. As shown, in preferred embodiments, such a semi-circular cross sectional profile is implemented in the form of a u-shaped cross-sectional profile. Similarly, in preferred embodiments, the circular bridge structure 165 has a u-shaped cross sectional profile and is connected to each one of the adjacent spaced apart annular structures 160 around an entire circumference thereof such that there are no openings between an exterior surface 170 and an interior surface 175 of the elastically deformable portion 125. Alternatively, the circular bridge structure 165 can be connected to each one of the adjacent spaced apart annular structures 160 at only certain discrete locations such that there are openings between the exterior surface 170 and the interior surface 175 of the elastically deformable portion 125.

There are several aspects of the elastically deformable portion 125 that influence its elastic deformation capability and causes the elastically deformable portion 125 to be a preferential location for such elastic deformation of the spine rod clamping body 105. One such aspect is that the circular bridge structure 165 is configured such that it transitions seamlessly into each one of the adjacent spaced apart annular structures 160. Such seamless transition refers to there being little or no discontinuity at a transition between the circular bridge structure 165 and each one of the adjacent spaced apart annular structures 160. Another such aspect is that the u-shaped cross sectional profile of the circular bridge structure 165 defines an inwardly curved face thereof that faces an opposite direction of an inwardly curved surface defined by the u-shaped cross-sectional profile of each one of the spaced apart annular structures 160. In this regard, the elastically deformable portion 125 can be embodied as length of "s-shaped bellows" connected between the spine rod mounting portion 115 and the bone screw connecting portion 120. Yet another such aspect is that a wall thickness of the u-shaped portion of each one of the spaced apart annular structures 160 and a wall thickness of the circular bridge structure 165 can be approximately the same. For example, the thin walls can be of similar or effectively identical thickness as compared to the wall thickness of other portions of the spine rod clamping body 105 being substantially thicker (e.g., 2-3 times thicker).

Figure 4:
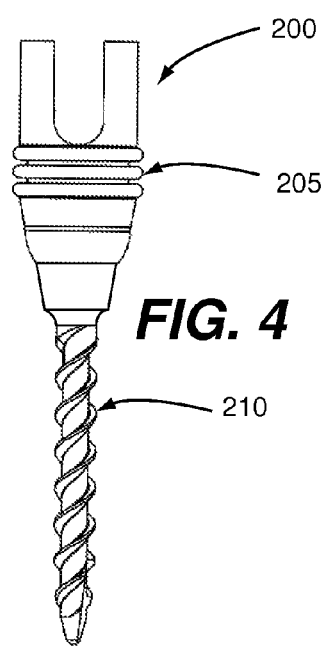
FIG. 4 is a side view of a rigid pedicle screw assembly configured in accordance with an embodiment of the present invention.

FIG. 4 shows a rigid pedicle screw assembly 200 configured in accordance with an embodiment of the present invention. Unlike common components of the polyaxial pedicle screw assembly 100 discussed above in reference to FIGS. 1-3, a spine rod clamping body 105 and a bone screw 210 of the rigid pedicle screw assembly 200 do not pivot or otherwise articulate relative to each other. In this regard, the spine rod clamping body 105 and the bone screw 210 are rigidly attached to each other.

In the preceding detailed description, reference has been made to the accompanying drawings that form a part hereof, and in which are shown by way of illustration specific embodiments in which the present invention may be practiced. These embodiments, and certain variants thereof, have been described in sufficient detail to enable those skilled in the art to practice embodiments of the present invention. It is to be understood that other suitable embodiments may be utilized and that logical, mechanical, chemical and electrical changes may be made without departing from the spirit or scope of such inventive disclosures. To avoid unnecessary detail, the description omits certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A spine rod clamping body for a pedicle screw assembly, comprising:
   a spine rod mounting;
   a bone screw connecting portion; and
   an elastically deformable portion connected between the spine rod mounting portion and the bone screw connecting portion, wherein the elastically deformable portion, the bone screw connecting portion and the spine rod mounting portion are all concentric about a common central axis, wherein the elastically deformable portion includes a plurality of spaced apart ring structures and a circular bridge structure, wherein each one of the spaced apart ring structures has a semi-circular cross sectional profile, wherein the circular bridge structure joins adjacent ones of the spaced apart ring structures such that adjacent ones of the spaced apart ring structures and the circular bridge structure therebetween jointly form a structure that is elastically deformable, wherein each one of the spaced apart ring structures and the circular bridge structure have a u-shaped cross-sectional profile such that the circular bridge structure and each adjacent one of the spaced apart ring structures form a respective S-shaped bellow structure, and wherein a size of the u-shaped cross-sectional profile of the circular bridge structure is substantially less than a size of the u-shaped cross-sectional profile of each adjacent one of the spaced apart ring structures.

2. The spine rod clamping body of claim 1 wherein:
   a central passage extends through the elastically deformable portion, the bone screw connecting portion and the spine rod mounting portion;
   a surface of the circular bridge structure that is within the central passage transitions seamlessly into a surface of each one of the adjacent spaced apart ring structures that is within the central passage; and
   the u-shaped cross sectional profile of the circular bridge structure defines an inwardly curved face thereof that faces an opposite direction of an inwardly curved surface defined by the u-shaped cross-sectional profile of each one of the spaced apart ring structures.

3. The spine rod clamping body of claim 1 wherein the elastically deformable portion, the bone screw connecting portion and the spine rod mounting portion are all formed as a one-piece structure from a single piece of material.

4. The spine rod clamping body of claim 1 wherein the circular bridge structure is connected to each one of the adjacent spaced apart ring structures around an entire circumference thereof.

5. The spine rod clamping body of claim 4 wherein:
   a central passage extends through the elastically deformable portion, the bone screw connecting portion and the spine rod mounting portion; and
   a surface of the circular bridge structure that is within central passage transitions seamlessly into a surface of each one of the adjacent spaced apart ring structures that is within the central passage; and
   the u-shaped cross sectional profile of the circular bridge structure defines an inwardly curved face thereof that faces an opposite direction of an inwardly curved surface defined by the u-shaped cross-sectional profile of each one of the spaced apart ring structures.

6. A pedicle screw assembly, comprising:
   a spine rod clamping body including a spine rod mounting portion, a bone screw connecting portion, and an elastically deformable portion between the spine rod mounting portion and the bone screw connecting portion, wherein the spine rod mounting portion has a spine rod receiving channel therein, wherein a central passage extends through the spine rod mounting portion, the bone screw connecting portion, and the elastically deformable portion, wherein the bone screw connecting portion includes a spherical seat within a surface thereof defined by the central passage, wherein the elastically deformable portion, the bone screw connecting portion and the spine rod mounting portion are all formed as a one-piece structure from a single piece of material and are all concentric about a common central axis, wherein the elastically deformable portion includes a plurality of spaced apart ring structures and a circular bridge structure joining adjacent ones of the ring such that adjacent ones of the spaced apart ring structures and the circular bridge structure therebetween jointly form a structure that elastically deforms when a bending moment is exerted between the spine rod mounting portion and the bone screw connecting portion, wherein each one of the spaced apart ring structures and the circular bridge structure each have a u-shaped cross-sectional profile such that the circular bridge structure and each adjacent one of the spaced apart ring structures form a respective S-shaped bellow structure, wherein a size of the u-shaped cross-sectional profile of the circular bridge structure is substantially less than a size of the u-shaped cross-sectional profile of each adjacent one of the spaced apart ring structures, wherein a wall thickness and shape of the u-shaped cross-sectional profile of the circular bridge structure and each adjacent one of the spaced apart ring structures are substantially the same, and wherein the u-shaped cross-sectional profile of the circular bridge structure defines an inwardly curved face thereof that faces an opposite direction of an inwardly curved surface defined by the u-shaped cross-sectional profile of each one of the spaced apart ring structures; and a bone screw having a first end portion and a second end portion, wherein the first end portion is within the central passage and includes a spherical head that is engaged with the spherical seat of the spine rod clamping body such that the bone screw is pivotably connected to the spine rod clamping body and wherein the second end portion defines a tip portion of the bone screw.

7. The pedicle screw assembly of claim 6 wherein:
a surface of the circular bridge structure that is within the central passage transitions seamlessly into a surface of each one of the adjacent spaced apart ring structures that is within the central passage.

8. The pedicle screw assembly of claim 6 wherein the circular bridge structure is connected each one of the adjacent spaced apart ring structures around an entire circumference thereof.

9. The pedicle screw assembly of claim 8 wherein:
a surface of the circular bridge structure that is within the central passage transitions seamlessly into a surface of each one of the adjacent spaced apart ring structures that is within the central passage.

10. A polyaxial pedicle screw assembly, comprising:
a spine rod clamping body including a spine rod mounting portion, a bone screw connecting portion, and an elastically deformable portion between the spine rod mounting portion and the bone screw connecting portion, wherein the elastically deformable portion, the bone screw connecting portion and the spine rod mounting portion are all formed as a one-piece structure from a single piece of material and are all concentric about a common central axis, wherein the elastically deformable portion includes a plurality of spaced apart annular structures and a circular bridge structure joining adjacent ones of the spaced apart annular structures such that adjacent ones of the spaced apart annular structures and the circular bridge structure therebetween jointly form a structure that elastically deforms when a bending moment is exerted between the spine rod mounting portion and the bone screw connecting portion, wherein each one of the spaced apart annular structures and the circular bridge structure each have a u-shaped cross-sectional profile such that the circular bridge structure and each adjacent one of the spaced apart annular structures form a respective S-shaped bellow structure, wherein a wall thickness and shape of the u-shaped cross-sectional profile of the circular bridge structure and each adjacent one of the spaced apart annular structures are substantially the same, wherein a size of the u-shaped cross-sectional profile of the circular bridge structure is substantially less than a size of the u-shaped cross-sectional profile of each adjacent one of the spaced apart annular structures, wherein the wall thickness the u-shaped cross-sectional profile of the circular bridge structure and each adjacent one of the spaced apart annular structures is not greater than one-third the thickness of adjacent portions of the spine rod clamping body, and wherein the u-shaped cross-sectional profile of the circular bridge structure defines an inwardly curved face thereof that faces an opposite direction of an inwardly curved surface defined by the u-shaped cross-sectional profile of each one of the spaced apart annular structures; and a bone screw having a tip portion and a head portion, wherein the head portion is pivotably coupled to the bone screw coupling portion of the spine rod clamping body.

11. The polyaxial pedicle screw assembly of claim 10 wherein:
a central passage extends through the elastically deformable portion, the bone screw connecting portion and the spine rod mounting portion; and
a surface of the circular bridge structure that is within the central passage transitions seamlessly into a surface of each one of the adjacent spaced apart annular structures that is within the central passage.

12. The polyaxial pedicle screw assembly of claim 10 wherein the circular bridge structure is connected each one of the adjacent spaced apart annular structures around an entire circumference thereof.

13. The polyaxial pedicle screw assembly of claim 12 wherein:
a central passage extends through the elastically deformable portion, the bone screw connecting portion and the spine rod mounting portion; and
a surface of the circular bridge structure that is within the central passage transitions seamlessly into a surface of each one of the adjacent spaced apart annular structures that is within the central passage.

* * * * *